US008871983B2

(12) United States Patent
Svetlov et al.

(10) Patent No.: US 8,871,983 B2
(45) Date of Patent: Oct. 28, 2014

(54) LIPID COMPOUNDS FOR SUPPRESSION OF TUMORIGENESIS

(75) Inventors: Stanislav I. Svetlov, Gainesville, FL (US); Anatoliy Vakulenko, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 840 days.

(21) Appl. No.: 13/057,793

(22) PCT Filed: Aug. 10, 2009

(86) PCT No.: PCT/US2009/053288
§ 371 (c)(1),
(2), (4) Date: Apr. 7, 2011

(87) PCT Pub. No.: WO2010/017550
PCT Pub. Date: Feb. 11, 2010

(65) Prior Publication Data
US 2011/0177108 A1    Jul. 21, 2011

Related U.S. Application Data

(60) Provisional application No. 61/087,305, filed on Aug. 8, 2008.

(51) Int. Cl.
*A61K 31/133*  (2006.01)
*C07C 217/28*  (2006.01)

(52) U.S. Cl.
CPC ............. *A61K 31/133* (2013.01); *C07C 217/28* (2013.01)
USPC ........................................................ 568/589

(58) Field of Classification Search
CPC .. C07C 217/28; A61K 31/045; A61K 31/075; A61K 31/133
USPC ........................................................ 568/589
See application file for complete search history.

(56) References Cited

U.S. PATENT DOCUMENTS

| 4,559,157 | A | 12/1985 | Smith et al. |
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |

FOREIGN PATENT DOCUMENTS

| CS | 275660 B6 | 3/1992 |
| EP | 0037780 | 10/1981 |
| JP | 57-028038 | 2/1982 |
| JP | H02-243658 A | 9/1990 |
| JP | H11-349478 A | 12/1999 |
| JP | 2003-12616 | 1/2003 |
| WO | WO 2004/078168 | 9/2004 |
| WO | WO 2005/074933 | 8/2005 |
| WO | WO 2007/119108 | 10/2007 |

OTHER PUBLICATIONS

Himber, J. et al. "Beta-adrenoceptor binding potencies of new aliphatic and alicyclic oxime ethers and their relevance to intraocular pressure control" *Methods and Findings in Experimental and Clinical Pharmacology*, 1989, pp. 315-321, vol. 11, No. 5.
Steiner, B. et al. "Preparation, characterization, and antimicrobial activity of 3-alkyl-5-decyloxymethyloxazolidines" *Chemical Papers*, 1992, pp. 202-206, vol. 46, No. 3.
Williams, D.B.G. et al. "Aluminium triflate: an efficient recyclable Lewis acid catalyst for the aminolysis of epoxides" *Tetrahedron Letters*, 2006, pp. 6557-6560, vol. 47, No. 37.
Azizi, N. et al. "Highly Chemoselective Addition of Amines to Epoxides in Water" *Organic Letters*, 2005, pp. 3649-3651, vol. 7, No. 17.
Shimogawa, H. etal. "A Wrench-Shaped Synthetic Molecule that Modulates a Transcription Factor-Coactivator Interaction" *Journal of the American Chemical Society*, 2004, pp. 3461-3471, vol. 126, No. 11.
Juyal, P. et al. "Alkyloxy Alkylamino Propanols as Multifunctional Fuel Stabilizers" *Petroleum Science and Technology*, 2001, pp. 411-424, vol. 19, Nos. 3&4.
CAPLUS Assession No. 1993:38813, Steiner, B. et al. "Preparation, characterization, and antimicrobial activity of 3-alkyl-5-decyloxymethyloxazolidines" *Chemical Papers*, 1992, pp. 202-206, vol. 46, No. 3. Abstract Only.
Sozzani, S. et al. "Propranolol, a Phosphatidate Phosphohydrolase Inhibitor, Also Inhibits Protein Kinase C" *The Journal of Biological Chemistry*, Oct. 5, 1992, pp. 20481-20488, vol. 267, No. 28.
CAPLUS Assession No. 1989:470331, Himber, J. et al. "Beta-adrenoceptor binding potencies of new aliphatic and alicyclic oxime ethers and their relevance to intraocular pressure control" *Methods and Findings in Experimental and Clinical Pharmacology*, 1989, pp. 315-321, vol. 11, No. 5. Abstract Only.
Bouzoubaa, M. et al. "Synthesis and β-Adrenergic Blocking Activity of New Aliphatic and Alicyclic Oxime Ethers" *Journal of Medicinal Chemistry*, 1984, pp. 1291-1294, vol. 27, No. 10.
Written Opinion in International Application No. PCT/US2009/053288, Mar. 31, 2010, pp. 1-6.

*Primary Examiner* — Yevegeny Valenrod
(74) *Attorney, Agent, or Firm* — Saliwanchik, Lloyd & Eisenschenk

(57) ABSTRACT

The present invention provides compounds, or pharmaceutically acceptable salts or analogs thereof, which exhibit anti-tumor activity. The present invention also includes methods for inhibiting the growth of cancer cells by contacting an effective amount of a compound of the present invention with the cancer cells in vitro or in vivo.

12 Claims, 11 Drawing Sheets

Fig. 6A
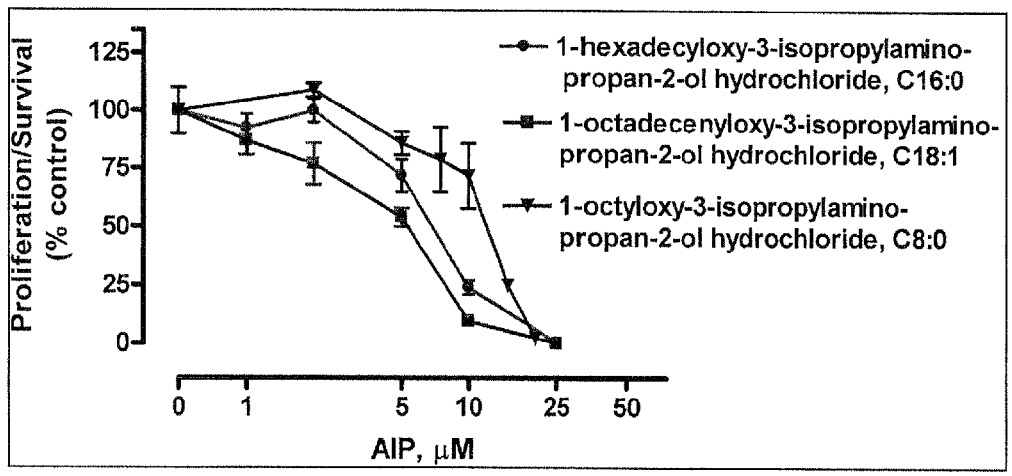
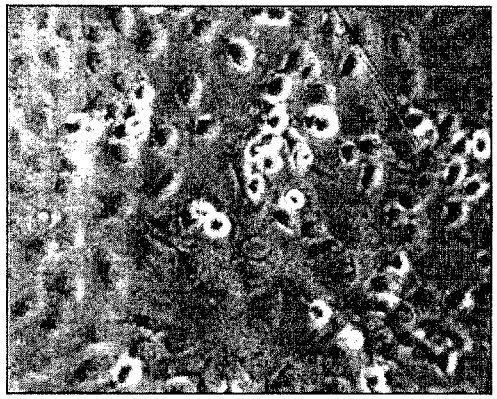
Fig. 6B
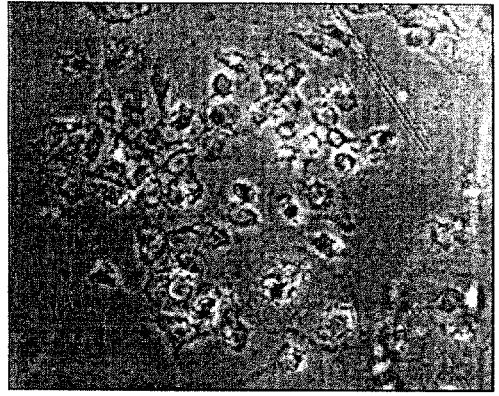
Fig. 6C

Fig. 7A
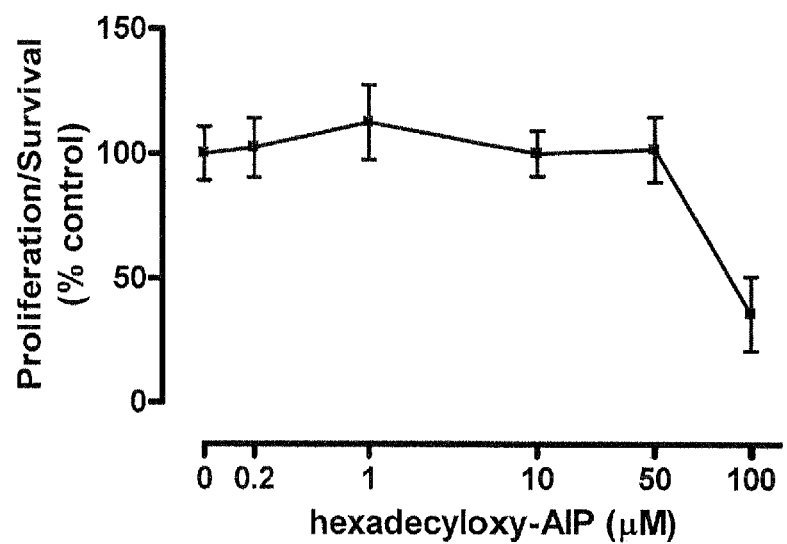
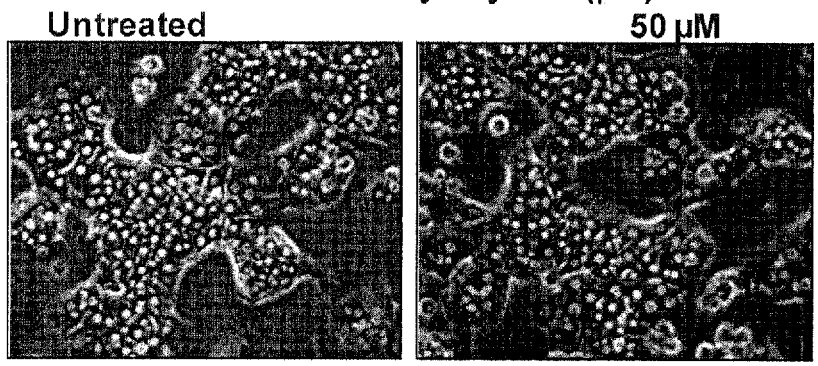
Fig. 7B            Fig. 7C

Fig. 8A
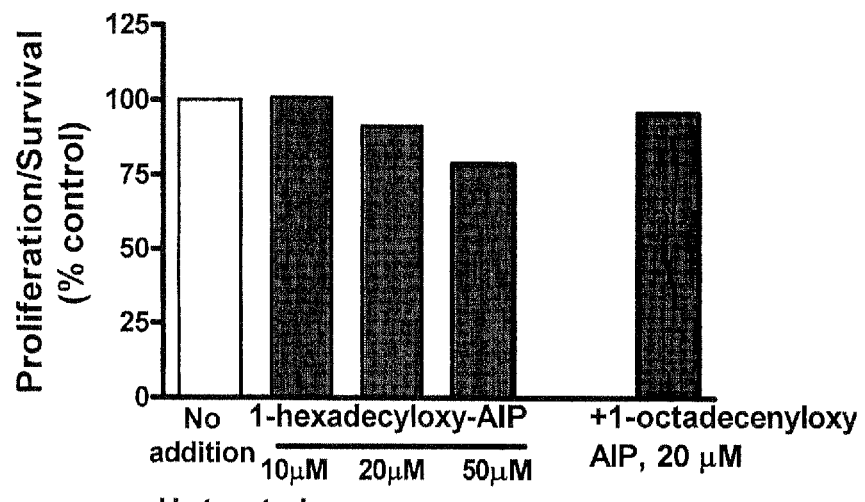
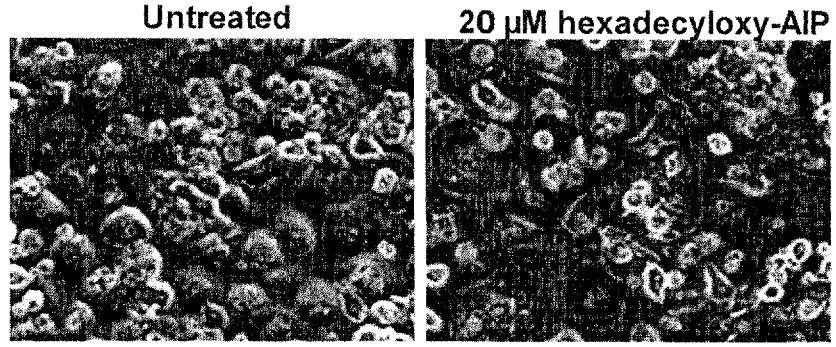
Fig. 8B    Fig. 8C

Control

20 µM

50 µM

Fig. 11B Control

LIPID COMPOUNDS FOR SUPPRESSION OF TUMORIGENESIS

This invention was made with government support under National Science Foundation grant number 1R21DK061649-01. The government has certain rights in the invention.

CROSS-REFERENCE TO RELATED APPLICATION

This application is the U.S. national stage application of International Patent Application No. PCT/US 2009/053288, filed Aug. 10, 2009, which claims the benefit of U.S. Provisional Application Ser. No. 61/087,305, filed Aug. 8, 2008, the disclosures of which are hereby incorporated by reference in their entirety, including all figures, tables and amino acid or nucleic acid sequences.

BRIEF SUMMARY

The present invention provides compounds, or pharmaceutically acceptable salts or analogs thereof, which exhibit anti-tumor activity. The present invention also includes methods for inhibiting the growth of cancer cells by contacting an effective amount of a compound of the present invention with the cancer cells in vitro or in vivo. By administering the compound of the present invention to a subject (e.g., a human or non-human animal), the invention provides a method for inhibiting the growth of cancer cells or treating cancer and other cell proliferation disorders in vivo. Optionally, the methods of the invention may comprise a step of diagnosing a subject with a cancer. Optionally, the methods of the invention may comprise a step of selecting a compound of the invention (or an analog, pharmaceutically-acceptable salt, or composition) with the purpose of employing the compound of the invention to inhibit the growth of cancer cells or otherwise treat cancer or another cell proliferation disorder. The invention also includes compositions comprising a compound of the present invention (or a pharmaceutically acceptable salt or analog thereof) and a pharmaceutically acceptable carrier.

Figure 1:
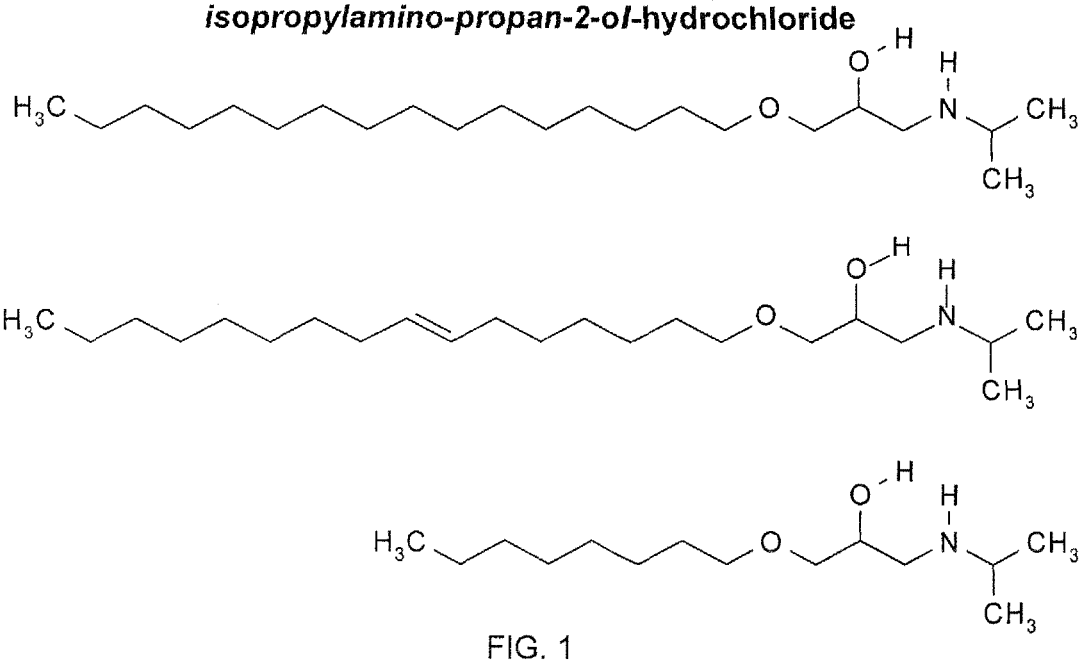
FIGS. 1-5: Chemical structures and mass spectra. Data for the respective figures is provided below.
Figure 2:
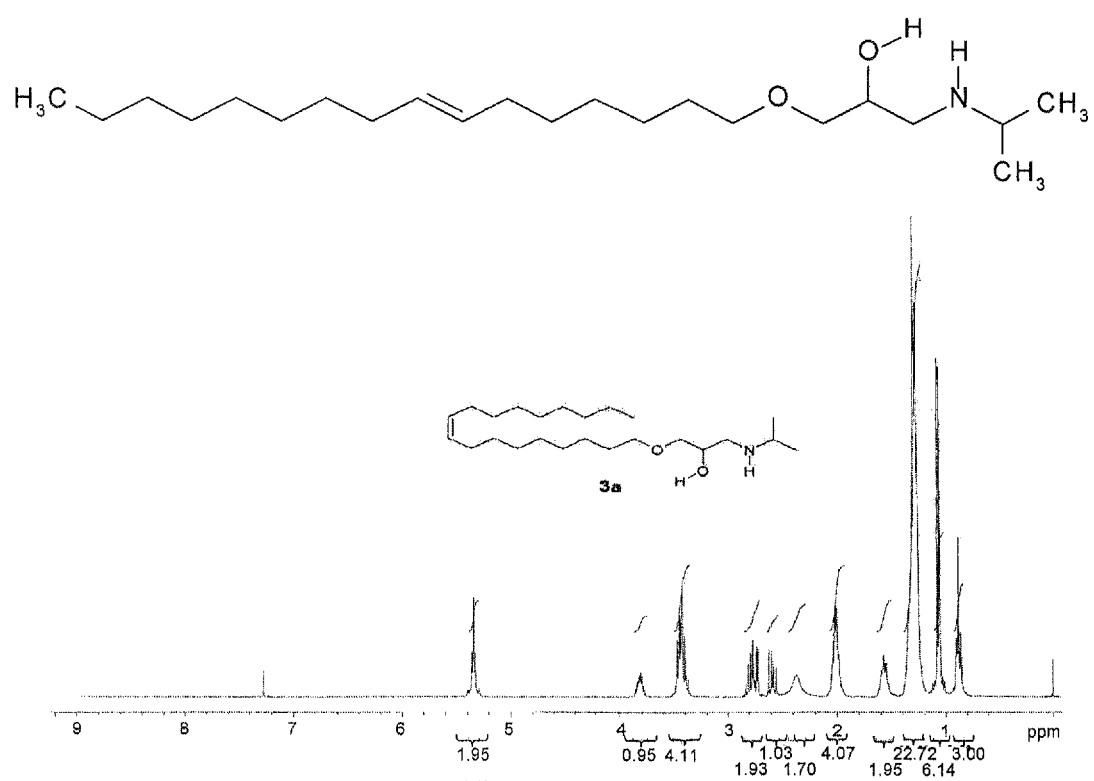
Figure 3:
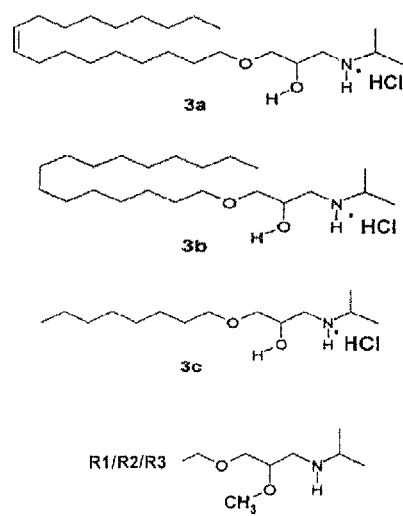

Data for FIG. 2

| INDEX | FREQUENCY | PPM | HEIGHT |
|---|---|---|---|
| 1 | 2183.268 | 7.276 | 8.1 |
| 2 | 1609.295 | 5.363 | 13.9 |
| 3 | 1604.076 | 5.346 | 30.9 |
| 4 | 1599.131 | 5.329 | 14.0 |
| 5 | 1152.616 | 3.841 | 5.0 |
| 6 | 1150.556 | 3.834 | 4.3 |
| 7 | 1148.633 | 3.828 | 6.4 |
| 8 | 1146.573 | 3.821 | 6.8 |
| 9 | 1144.650 | 3.815 | 6.5 |
| 10 | 1142.590 | 3.808 | 7.3 |
| 11 | 1140.667 | 3.801 | 4.4 |
| 12 | 1138.607 | 3.795 | 6.3 |
| 13 | 1134.486 | 3.781 | 3.3 |
| 14 | 1045.623 | 3.485 | 3.3 |
| 15 | 1041.777 | 3.472 | 17.7 |
| 16 | 1036.283 | 3.454 | 27.6 |
| 17 | 1035.185 | 3.450 | 27.0 |
| 18 | 1032.026 | 3.439 | 24.5 |
| 19 | 1027.768 | 3.425 | 34.0 |
| 20 | 1020.626 | 3.401 | 18.8 |
| 21 | 1016.917 | 3.389 | 6.5 |
| 22 | 1010.874 | 3.369 | 5.4 |
| 23 | 850.178 | 2.833 | 3.7 |
| 24 | 843.997 | 2.813 | 9.9 |
| 25 | 837.680 | 2.792 | 13.7 |
| 26 | 831.774 | 2.772 | 17.6 |
| 27 | 828.203 | 2.760 | 10.1 |
| 28 | 825.181 | 2.750 | 5.1 |
| 29 | 820.099 | 2.733 | 15.6 |
| 30 | 816.253 | 2.720 | 14.7 |
| 31 | 786.861 | 2.622 | 14.5 |
| 32 | 778.895 | 2.596 | 14.0 |
| 33 | 774.912 | 2.582 | 9.5 |
| 34 | 766.946 | 2.556 | 8.9 |
| 35 | 711.183 | 2.370 | 6.6 |
| 36 | 606.250 | 2.020 | 28.2 |
| 37 | 600.619 | 2.002 | 27.8 |
| 38 | 594.301 | 1.981 | 13.0 |
| 39 | 478.654 | 1.595 | 8.0 |
| 40 | 472.062 | 1.573 | 12.9 |
| 41 | 465.194 | 1.550 | 10.4 |
| 42 | 458.602 | 1.528 | 4.0 |
| 43 | 387.868 | 1.293 | 151.2 |
| 44 | 380.863 | 1.269 | 123.2 |
| 45 | 336.775 | 1.122 | 4.2 |
| 46 | 330.457 | 1.101 | 4.9 |
| 47 | 323.040 | 1.077 | 105.6 |
| 48 | 316.860 | 1.056 | 102.9 |
| 49 | 309.306 | 1.031 | 6.0 |
| 50 | 302.988 | 1.010 | 4.8 |
| 51 | 270.711 | 0.902 | 18.1 |
| 52 | 264.393 | 0.881 | 49.8 |
| 53 | 257.388 | 0.858 | 19.6 |
| 54 | 250.658 | 0.835 | 2.7 |
| 55 | 0.000 | 0.000 | 11.5 |

Figure 4:
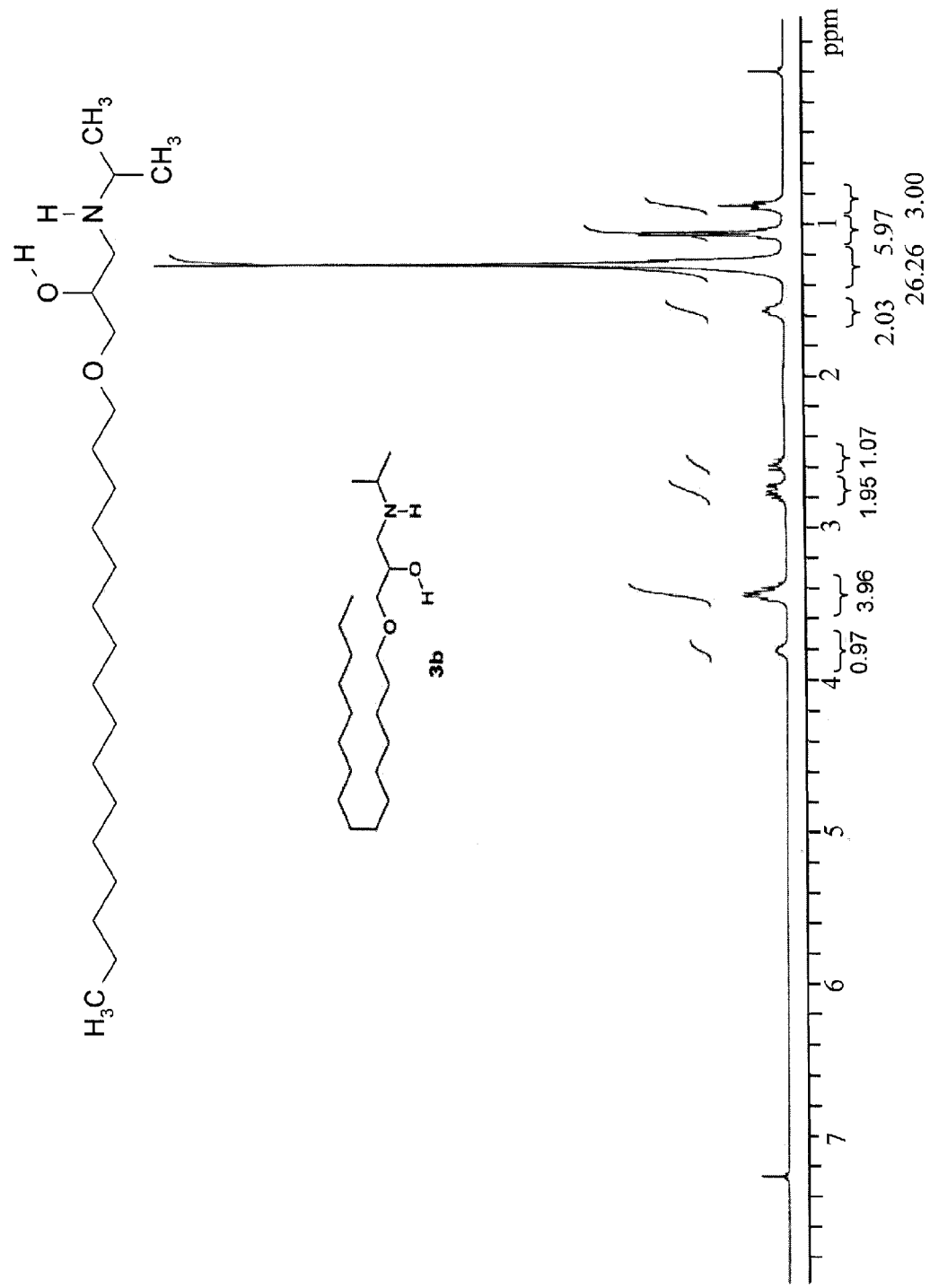

Data for FIG. 4

| INDEX | FREQUENCY | PPM | HEIGHT |
|---|---|---|---|
| 1 | 2180.933 | 7.268 | 7.3 |
| 2 | 1150.144 | 3.833 | 2.2 |
| 3 | 1146.161 | 3.820 | 2.7 |
| 4 | 1143.963 | 3.812 | 3.0 |
| 5 | 1142.178 | 3.806 | 2.9 |
| 6 | 1140.118 | 3.800 | 2.9 |
| 7 | 1136.272 | 3.787 | 2.4 |
| 8 | 1043.563 | 3.478 | 6.8 |
| 9 | 1037.107 | 3.456 | 10.8 |
| 10 | 1035.459 | 3.451 | 11.4 |
| 11 | 1033.811 | 3.445 | 9.9 |
| 12 | 1029.553 | 3.431 | 11.2 |
| 13 | 1026.394 | 3.421 | 8.6 |
| 14 | 1020.214 | 3.400 | 6.5 |
| 15 | 1016.643 | 3.388 | 2.7 |
| 16 | 1010.462 | 3.367 | 2.1 |
| 17 | 842.075 | 2.806 | 3.6 |
| 18 | 835.894 | 2.786 | 5.1 |
| 19 | 831.362 | 2.771 | 4.5 |
| 20 | 829.576 | 2.765 | 4.9 |
| 21 | 827.791 | 2.759 | 3.9 |
| 22 | 823.395 | 2.744 | 2.8 |
| 23 | 819.687 | 2.732 | 5.0 |
| 24 | 815.841 | 2.719 | 4.5 |
| 25 | 786.586 | 2.621 | 4.5 |
| 26 | 778.758 | 2.595 | 4.5 |
| 27 | 774.637 | 2.582 | 3.2 |
| 28 | 766.808 | 2.555 | 2.8 |
| 29 | 478.517 | 1.595 | 3.9 |
| 30 | 472.336 | 1.574 | 5.7 |

-continued

Data for FIG. 4

| INDEX | FREQUENCY | PPM | HEIGHT |
|---|---|---|---|
| 31 | 465.744 | 1.552 | 4.7 |
| 32 | 459.426 | 1.531 | 2.1 |
| 33 | 381.550 | 1.272 | 55.2 |
| 34 | 376.468 | 1.255 | 165.8 |
| 35 | 370.974 | 1.236 | 35.8 |
| 36 | 327.298 | 1.091 | 7.0 |
| 37 | 321.804 | 1.072 | 38.1 |
| 38 | 315.761 | 1.052 | 37.4 |
| 39 | 310.130 | 1.034 | 6.9 |
| 40 | 270.299 | 0.901 | 8.5 |
| 41 | 264.118 | 0.880 | 17.0 |
| 42 | 257.388 | 0.858 | 7.9 |
| 43 | 0.000 | 0.000 | 9.1 |

Figure 5:
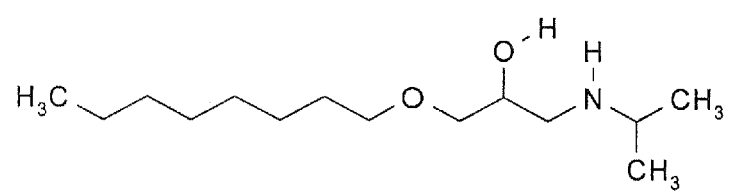
Figure 5:
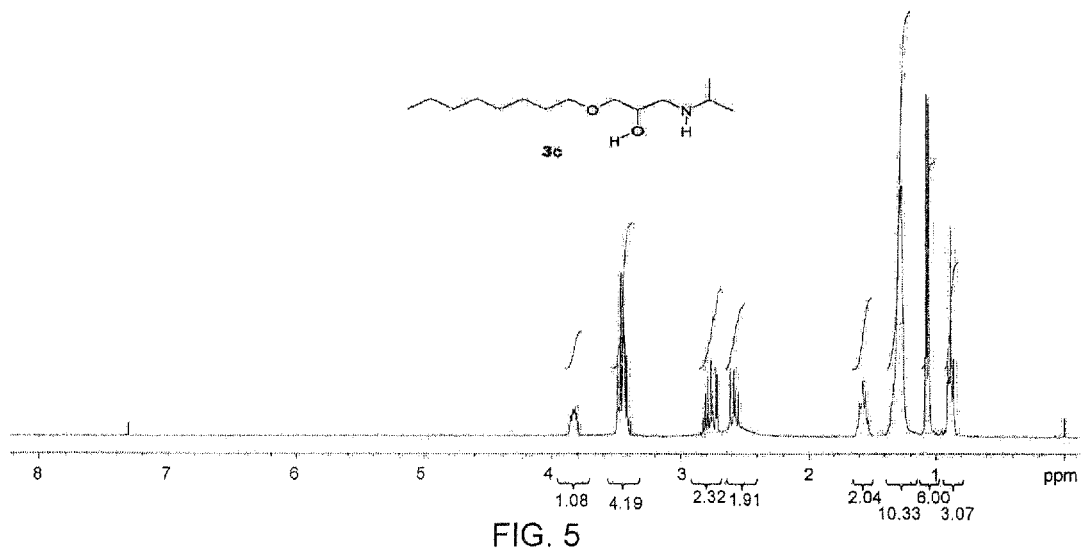
Figure 9A:
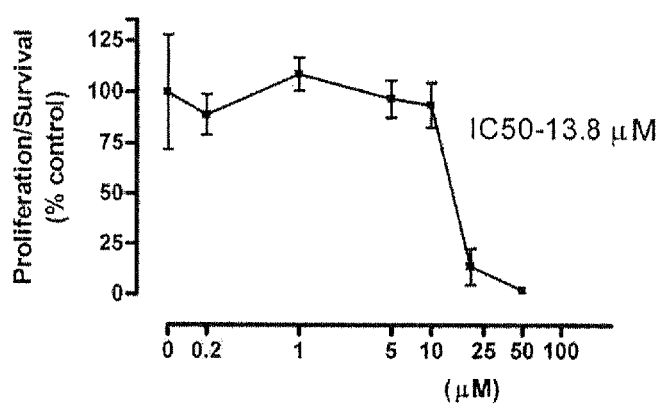
Figure 9B:
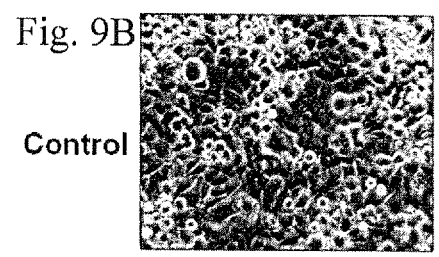
Figure 9C:
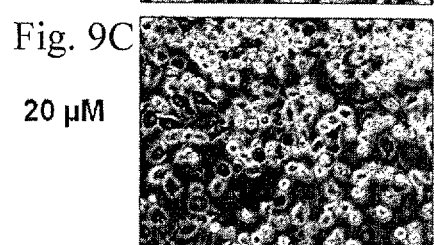
Figure 9D:
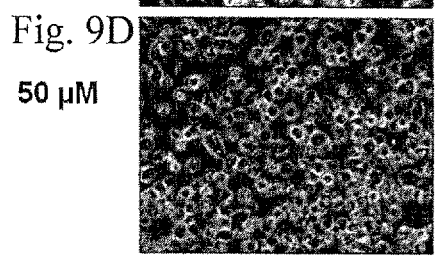
Figure 10A:
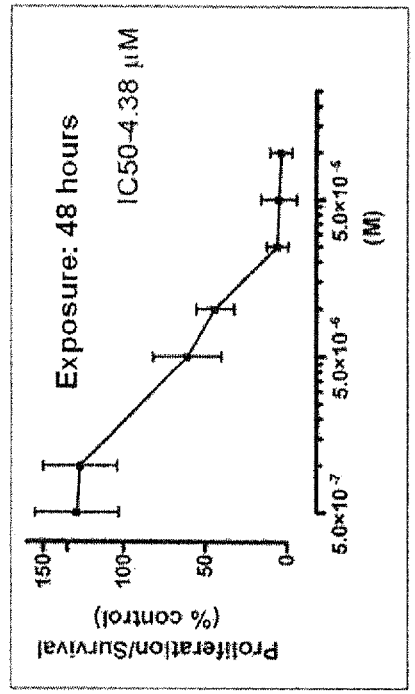
Figure 10B:
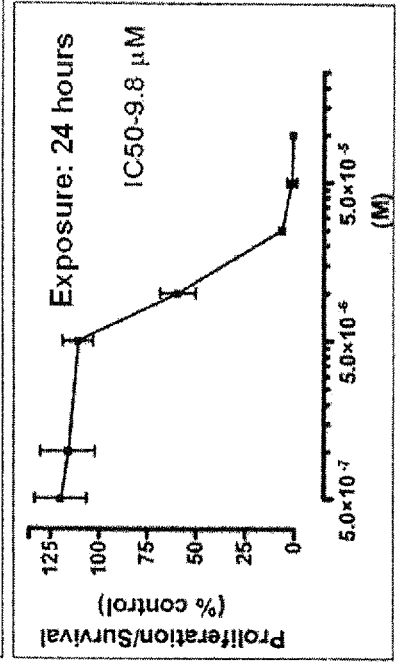
Figure 10C:
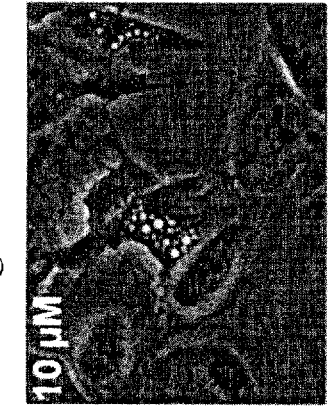
Figure 10D:
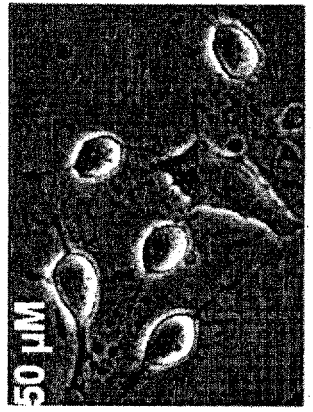
Figure 10E:
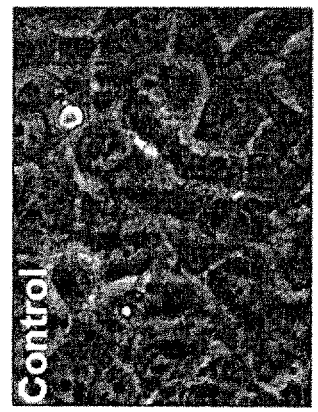
Figure 10F:
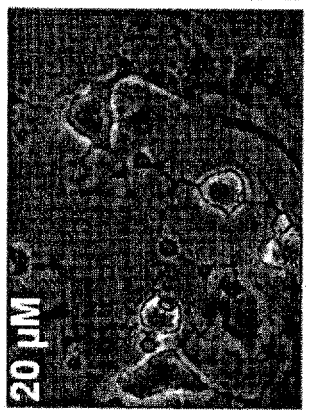
Figure 11A:
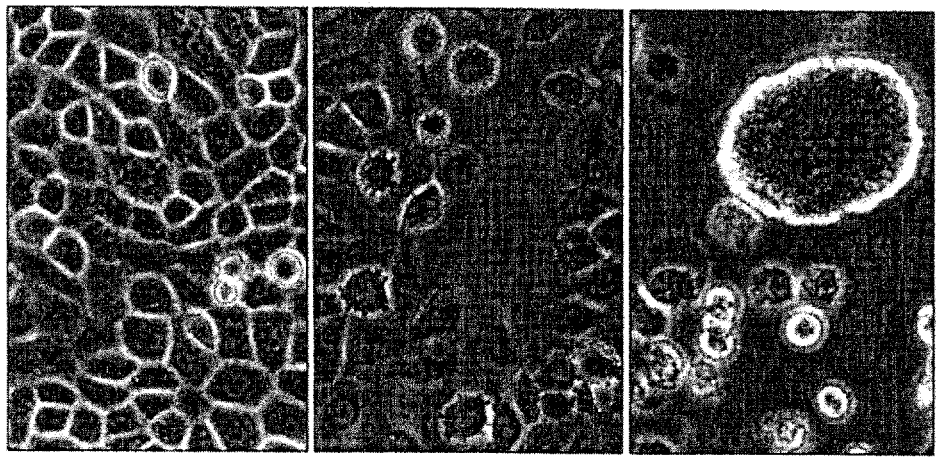
Figure 11A:
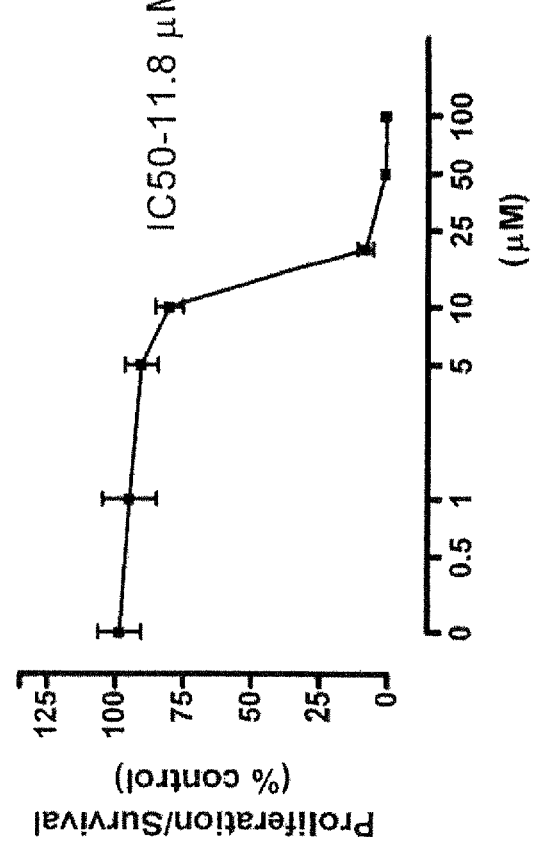

Data for FIG. 5

| INDEX | FREQUENCY | PPM | HEIGHT |
|---|---|---|---|
| 1 | 2192.059 | 7.305 | 4.1 |
| 2 | 1159.621 | 3.865 | 3.5 |
| 3 | 11.55.501 | 3.851 | 6.2 |
| 4 | 1153.578 | 3.844 | 5.8 |
| 5 | 1151.380 | 3.837 | 8.3 |
| 6 | 1149.595 | 3.831 | 8.2 |
| 7 | 1147.397 | 3.824 | 7.6 |
| 8 | 1145.474 | 3.817 | 9.1 |
| 9 | 1143.139 | 3.810 | 5.3 |
| 10 | 1141.491 | 3.804 | 7.1 |
| 11 | 1137.233 | 3.790 | 3.9 |
| 12 | 1042.189 | 3.473 | 21.6 |
| 13 | 1039.442 | 3.464 | 8.7 |
| 14 | 1035.459 | 3.451 | 48.5 |
| 15 | 1029.416 | 3.431 | 43.4 |
| 16 | 1026.806 | 3.422 | 35.1 |
| 17 | 1025.296 | 3.417 | 30.1 |
| 18 | 1020.763 | 3.402 | 23.7 |
| 19 | 1017.055 | 3.389 | 5.0 |
| 20 | 1011.011 | 3.369 | 4.6 |
| 21 | 848.942 | 2.829 | 5.3 |
| 22 | 842.624 | 2.808 | 13.0 |
| 23 | 836.443 | 2.788 | 17.7 |
| 24 | 829.988 | 2.766 | 22.7 |
| 25 | 825.868 | 2.752 | 13.4 |
| 26 | 824.082 | 2.746 | 7.3 |
| 27 | 817.764 | 2.725 | 20.6 |
| 28 | 814.056 | 2.713 | 18.6 |
| 29 | 784.252 | 2.614 | 20.1 |
| 30 | 776.148 | 2.587 | 19.9 |
| 31 | 772.302 | 2.574 | 14.2 |
| 32 | 764.199 | 2.547 | 13.6 |
| 33 | 479.066 | 1.597 | 10.1 |
| 34 | 472.062 | 1.573 | 16.5 |
| 35 | 465.194 | 1.550 | 13.5 |
| 36 | 458.464 | 1.528 | 4.9 |
| 37 | 386.632 | 1.288 | 67.5 |
| 38 | 381.550 | 1.272 | 74.5 |
| 39 | 323.178 | 1.077 | 102.0 |
| 40 | 322.079 | 1.073 | 101.3 |
| 41 | 316.997 | 1.056 | 100.1 |
| 42 | 315.761 | 1.052 | 98.3 |
| 43 | 270.574 | 0.902 | 20.8 |
| 44 | 264.118 | 0.880 | 62.6 |
| 45 | 257.251 | 0.857 | 22.9 |
| 46 | −0.000 | −0.000 | 5.6 |

FIGS. 6A-C. Inhibition of proliferation/survival of HUH-7 human hepatocarcinoma cells in culture upon 24 h single treatment with different doses of AIPs. Upper panel (FIG. 6A): dose-response curves; lower panel: cell culture microphotographs (20×). FIG. 6B shows untreated HUH-7 cells and FIG. 6C shows HUH-7 cells treated with 20 μM hexadecylcycloxy-AIP.

FIGS. 7A-C. Survival/proliferation of primary rat hepatocytes 24 hours after single treatment with hexadecyl-AIP. Upper panel (FIG. 7A): dose-response; lower panels: microphotograph (10×) for untreated (FIG. 7B) and treated cells (treated with 50 μM hexadecylcycloxy-AIP; FIG. 7C).

FIGS. 8A-C. Lack of significant effect of hexadecyloxy and octadecenyloxy-AIPs on survival and proliferation of human primary hepatocytes. Upper panel (FIG. 8A): dose-response; lower panel: microphotograph (20×) for untreated (FIG. 8B) and treated cells (treated with 20μM hexadecylcycloxy-AIP; FIG. 8C).

FIGS. 9A-D. Effects of 1-hexadecyloxy-3-isopropylamino-propan-2-ol on breast cancer cells. Photomicrographs of untreated and treated cells are provided in FIGS. 9B-D).

FIGS. 10A-F. Effects of 1-hexadecyloxy-3-isopropylamino-propan-2-ol on human osteosarcoma cells (at 48 hours exposure (FIG. 10A) and 24 hours exposure (FIG. 10B)). Photomicrographs of untreated and treated cells are provided in FIGS. 10C-F.

FIGS. 11A-D. Effects of 1-hexadecyloxy-3-isopropylamino-propan-2-ol on canine osteosarcoma cells. Photomicrographs of untreated and treated cells are provided in FIGS. 11B-D.

DETAILED DISCLOSURE OF THE INVENTION

The subject invention pertains to compounds capable of treating cancer. In some embodiments, cancer cell growth inhibition may be achieved via the contacting of cells with components disclosed herein. In some embodiments, the compounds of the invention may act as antagonists of certain LPL-GPCRs such as G2A, GPR4, and ORG-1 and/or lipid metabolism enzyme(s) such as sphingosine kinase (SPK).

In one aspect, the subject invention concerns a pharmaceutical composition comprising compounds of Formula I or a pharmaceutically acceptable salt thereof.

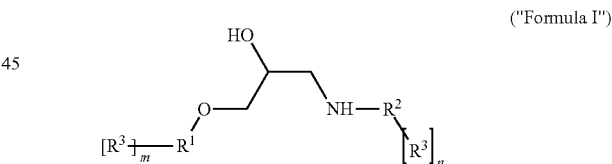

("Formula I")

Preferably $R^1$ and $R^2$ are aliphatic (including, in some embodiments, alicyclic). Preferably $R^1$ is $C_1$-$C_{30}$, and $R^1$ can have 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms.

In certain embodiments, $R^1$ contains no cyclic moieties. In other embodiments, $R^1$ is straight-chain. In yet other embodiments, $R^1$ is branched-chain or a non-aromatic cyclic.

$R^2$ can contain in some embodiments, no cyclic moieties. In certain other embodiments, $R^2$ is straight-chain or branched-chain. Yet other embodiments provide $R^2$ as a non-aromatic cyclic.

In certain embodiments, in and n are independently 0-3, and each substituent $R^3$ that is present can independently contain 1-10 non-hydrogen atoms along with 0 or more hydrogen atoms. In determining whether a particular atom is deemed to belong to $R^1$ or $R^2$, on the one hand, or $R^3$ on the other hand, if the particular atom falls within the scope of $R^1$ or $R^2$, then it is deemed to belong to $R^1$ or $R^2$ and not to $R^3$. For example, in an embodiment where $R^2$ is aliphatic, in the molecule

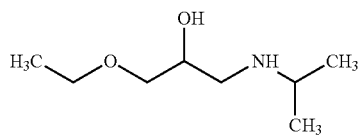

the $R^2$ group is deemed to be isopropyl with n=0, rather than $R^2$=substituted ethyl, n=1, and $R^3$ on $R^2$ is methyl. The entire isopropyl group is aliphatic and so is deemed to belong entirely to $R^2$. On the other hand, in the molecule

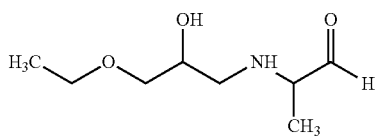

the aldehyde (formyl) group is not aliphatic, and so $R^2$ is substituted ethyl, n=1, and $R^3$ on $R^2$ is CH=O. In all cases, the atom belonging to $R^3$ that is directly bonded to $R^2$ must be (a) a carbon that is itself directly bonded to a heteroatom in $R^3$, for example a carbonyl carbon; (b) a heteroatom, for example halogen, O, S, P, or N; or (c) a carbon that is a ring atom in an aryl or heteroaryl ring.

In certain embodiments, the compound of the invention is

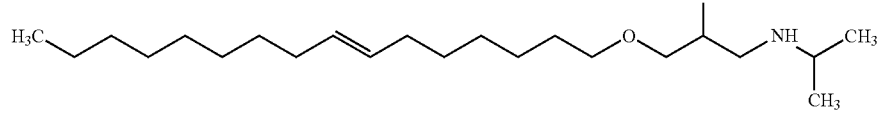

"Compound A" (trans or cis); or

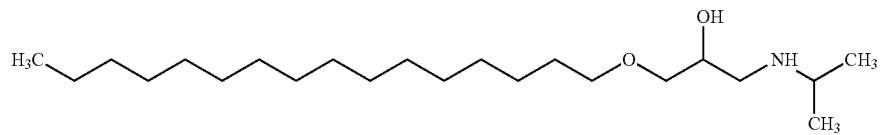 [SMILES: CCCCCCCCCCCCCCCCOCC(O)CNC(C)C]

"Compound B"; or

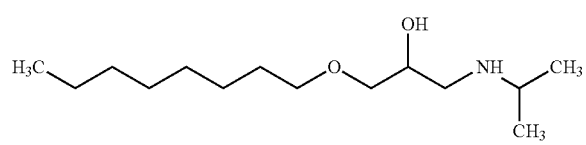

"Compound C".

In certain compositions and methods of the invention, a combination of any two of these compounds may be used, or a combination of all three may be used. Likewise, a combination of the salts could be used. Moreover, it is appreciated that each depicted compound A, B, and C may exist in more than one stereoisomeric form, including E and Z configurations at double bonds and isomers in which any given chiral center may be (R) or (S), and it is contemplated that any single isomer may be used or any mixture or combination thereof.

More specifically, it is to be understood that the compounds disclosed herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is understood that the disclosure of a compound herein encompasses any racemic, optically active, polymorphic, or stereoisomeric form, or mixtures thereof, which preferably possesses the useful properties described herein, it being well known in the art how to prepare optically active forms and how to determine activity using the standard tests described herein, or using other similar tests which are well known in the art.

In another aspect, the subject invention concerns a method of inhibiting the growth of cancer cells in a patient by the administration of an effective amount of a compound of the invention or a pharmaceutical composition comprising a compound of the invention. Preferably, an effective amount of a pure or isolated compound is administered. The method of the subject invention is useful in treating cancer and/or inhibiting tumor growth. Treatment of cancer involves a beneficial change in one or more symptoms associated with the particular cancer. Preferably, the treatment involves a decrease in tumor growth rate or a reduction in tumor mass or size.

According to the method of the subject invention, a substituted amino-propanol compound, or a pharmaceutically acceptable salt or analog thereof, is administered to a patient in an effective amount to treat the cancer. The substituted amino-propanol compound, or a pharmaceutically acceptable salt or analog thereof, can be administered prophylactically before tumor onset, or as treatment for existing tumors.

The precise dosage will depend on a number of clinical factors, for example, the type of patient (such as human, non-human mammal, or other animal), age of the patient, and the particular cancer under treatment and its aggressiveness. A person having ordinary skill in the art would readily be able to determine, without undue experimentation, the appropriate dosages required to achieve the appropriate clinical effect.

A "patient" refers to a human, non-human mammal, or other animal in which the administration of a compound, as disclosed herein, would have a beneficial effect.

As used herein, the term "treatment" includes amelioration or alleviation of a pathological condition associated with cancer and/or one or more symptoms thereof or reducing tumor mass or volume as a result of the administration of the compounds disclosed herein.

The substituted amino-propanol compounds of the subject invention, including Compounds A, B, and C with their associated stereoisomers, and analogs or derivatives of the foregoing, can be obtained through a variety of methods known in the art. Derivatives of the subject invention can be synthesized using methods of organic synthesis known to those of ordinary skill in the art.

A further aspect of the present invention provides a method of modulating the signaling activity of LPL-GPCRs such as G2A, GPR4, and ORG-1, and includes the step of contacting cells or tissue with an effective amount of a substituted amino-propanol compound, thereby modulating signal transduction through one or more LPL-GPCRs. The compounds of the invention can also be used to inhibit or reduce the activity of sphinosine kinase and cause apoptosis of tumor/cancer cells. These methods can be carried out in vivo or in vitro.

While the substituted amino-propanol compound can be administered as an isolated compound, it is preferred to administer these compounds as a pharmaceutical composition. The subject invention thus further provides pharmaceutical compositions comprising a substituted amino-propanol compound, as an active agent, or physiologically acceptable salt(s) thereof, in association with at least one pharmaceutically acceptable carrier or diluent. The pharmaceutical composition can be adapted for various routes of administration, such as enteral, parenteral, intravenous, intramuscular, topical, subcutaneous, and so forth. The substituted amino-propanol compound can be administered locally, at the site of the cancerous cells (e.g., intratumorally), or systemically. Administration can be continuous or at distinct intervals, as can be determined by a person of ordinary skill in the art. For example, but without limitation, administration may be at a frequency of 1, 2, 3, 4, 5, 6, 7, 8, 9, 10, 11, or 12 times every 1, 2, 3, 4, 5, or 6 months; 1, 2, 3, 4, 5, 6, 7, 8, 9, 10, 11, or 12 times every 1, 2, 3, 4, 5, or 6 weeks; 1, 2, 3, 4, 5, 6, 7, 8, 9, 10, 11, or 12 times every 1, 2, 3, 4, 5, or 6 days; 1, 2, 3, 4, 5, 6, 7, 8, 9, 10, 11, or 12 times every 1, 2, 3, 4, 5, or 6 hours; or at similar frequencies.

The compounds of the subject invention can be formulated according to known methods for preparing pharmaceutically useful compositions. Formulations are described in a number of sources which are well known and readily available to those skilled in the art. For example, *Remington's Pharmaceutical Science* (Martin E. W., Easton Pa., Mack Publishing Company, 19$^{th}$ ed., 1995) describes formulations which can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The substituted amino-propanol compounds of the present invention include all hydrates and salts that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including chloride, sulfate, nitrate, bicarbonate, and carbonate salts. Pharmaceutically acceptable salts may be obtained by using standard procedures well known in the art, for example by reacting a basic group such as an amine with an acid affording a physiologically acceptable anion or by reacting an acidic group such as a carboxylic acid with a base affording a physiologically acceptable cation. For example, alkali metal (e.g., lithium, sodium, potassium) and alkaline earth metal (e.g., magnesium, calcium) salts of carboxylic acids are commonly used. Physiologically acceptable cations and anions are well known in the art.

The compounds of the present invention can be formulated as pharmaceutical compositions and administered to a subject, such as a human or veterinary patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations may contain less than 0.01%, 0.01-0.05%, 0.05-0.1%, 0.1-0.5%, 0.5-1.0%, 1.0-5.0%, 5-10%, 10-20%, 20-30%, 30-40%, 40-50%, or greater than 50% active ingredient by weight, or any combination of such ranges. The amount of the active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

According to the method of the subject invention, a substituted amino-propanol compound can be administered locally, at the site of cancer cells. For example, the substituted amino-propanol compound or composition can be directly administered to a tumor (e.g., topically or injected into the tumor).

The active agent (i.e., substituted amino-propanol compound or pharmaceutically acceptable salts thereof) may also be administered intravenously or intraperitoneally by infusion or injection. Dispersions and/or solutions of the active agent or its salts can be prepared in water, preferably mixed with a nontoxic surfactant, in oils, or in glycerol, liquid polyethylene glycols, triacetin, and in mixtures thereof. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds of the invention may be applied in pure-form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising substituted amino-propanol compound or pharmaceutically acceptable salts thereof, as described herein, or pharmaceutically acceptable salts thereof, in combination with a pharmaceutically acceptable carrier. Pharmaceutical compositions adapted for oral, topical or parenteral administration, comprising an amount of substituted amino-propanol compound, or a pharmaceutically acceptable salt thereof, constitute a preferred embodiment of the invention. The dose administered to a subject, particularly a human, in the context of the present invention should be sufficient to effect a therapeutic response in the patient over a reasonable time frame. One skilled in the art will recognize that dosage will depend upon a variety of factors including the condition of the animal, the body weight of the animal, as well as the severity and stage of the cancer.

Mammalian species which benefit from the disclosed methods for the inhibition of cancer cell growth, include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used herein interchangeably and are intended to include such human and non-human mammalian species. Likewise, in vitro methods of the present invention can be carried out on cells of such mammalian species.

The methods of the present invention, for example, for inhibiting the growth of a cancerous cell, can be advantageously combined with at least one additional therapeutic method, including but not limited to chemotherapy, radiation therapy, therapy that selectively inhibits Ras oncogenic signaling, or any other therapy known to those of skill in the art of the treatment and management of cancer, such as administration of an anti-cancer agent. Moreover, the methods of the present invention may be advantageously combined with known analytical techniques for diagnosing or monitoring the course of a cancer patient, such as biopsy or imaging techniques such as ultrasound, X-ray, MRI, PET, or CAT, such that initial administration or further administration of a compound, salt, analog, or composition of the invention is conditional upon the results of the analytical technique(s). For example, in some embodiments, a further administration may be conditioned upon analysis that indicates that cancer cell growth has been inhibited by one or more initial administrations. Likewise, in some embodiments, an initial administration may be conditioned upon analysis that indicates that a cancer has not responded sufficiently to some alternative therapy.

According to the method of the subject invention, a substituted amino-propanol compound or a pharmaceutically acceptable salt or derivative thereof can be administered to a patient by itself, or co-administered with one or more other compounds, including one or more other substituted amino-propanol compounds, or a pharmaceutically acceptable salt or analog thereof. Co-administration can be carried out simultaneously (in the same or separate formulations) or consecutively. Furthermore, according to the method of the subject invention, the substituted amino-propanol compound, or a pharmaceutically acceptable salt or analog thereof, can be administered to a patient as adjunctive therapy. For example, a substituted amino-propanol compound, or a pharmaceutically acceptable salt or analog thereof, can be administered to a patient in conjunction with radiation therapy or chemotherapy.

Thus, the substituted amino-propanol compounds of the subject invention, whether administered separately, or as a pharmaceutical composition, can include various other components as additives. Examples of acceptable components or adjuncts which can be employed in relevant circumstances include chemotherapeutic agents, anti-proliferative agents, anti-mitotic agents, anti-metabolite drugs, alkylating agents, drugs with target topoisomerases, drugs which target signal transduction in tumor cells, gene therapy, antisense agents, interfering RNA (RNAi), antibody therapeutics, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, steroid analogues, and corticosteroids. Examples of chemotherapeutic agents are listed in Table 1. Such components can provide additional therapeutic benefit, act to affect the therapeutic action of the substituted amino-propanol compound, or act towards preventing any potential side effects which may be posed as a result of administration of the substituted amino-propanol compound. The substituted amino-propanol compounds of the subject invention can be conjugated to a therapeutic agent, as well.

TABLE 1

Examples of Chemotherapeutic Agents

| | | |
|---|---|---|
| 13-cis-Retinoic Acid | 2-Amino-6-Mercaptopurine | 2-CdA |
| 2-Chlorodeoxyadenosine | 5-fluorouracil | 5-FU |
| 6-TG | 6-Thioguanine | 6-Mercaptopurine |
| 6-MP | Accutane | Actinomycin-D |
| Adriamycin | Adrucil | Agrylin |
| Ala-Cort | Aldesleukin | Alemtuzumab |
| Alitretinoin | Alkaban-AQ | Alkeran |
| All-transretinoic acid | Alpha interferon | Altretamine |
| Amethopterin | Amifostine | Aminoglutethimide |
| Anagrelide | Anandron | Anastrozole |
| Arabinosylcytosine | Ara-C | Aranesp |
| Aredia | Arimidex | Aromasin |
| Arsenic trioxide | Asparaginase | ATRA |
| Avastin | BCG | BCNU |
| Bevacizumab | Bexarotene | Bicalutamide |
| BiCNU | Blenoxane | Bleomycin |
| Bortezomib | Busulfan | Busulfex |
| C225 | Calcium Leucovorin | Campath |
| Camptosar | Camptothecin-11 | Capecitabine |
| Carac | Carboplatin | Carmustine |
| Carmustine wafer | Casodex | CCNU |
| CDDP | CeeNU | Cerubidine |

TABLE 1-continued

Examples of Chemotherapeutic Agents

| | | |
|---|---|---|
| cetuximab | Chlorambucil | Cisplatin |
| Citrovorum Factor | Cladribine | Cortisone |
| Cosmegen | CPT-11 | Cyclophosphamide |
| Cytadren | Cytarabine | Cytarabine liposomal |
| Cytosar-U | Cytoxan | Dacarbazine |
| Dactinomycin | Darbepoetin alfa | Daunomycin |
| Daunorubicin | Daunorubicin hydrochloride | Daunorubicin liposomal |
| DaunoXome | Decadron | Delta-Cortef |
| Deltasone | Denileukin diftitox | DepoCyt |
| Dexamethasone | Dexamethasone acetate | dexamethasone sodium phosphate |
| Dexasone | Dexrazoxane | DHAD |
| DIC | Diodex | Docetaxel |
| Doxil | Doxorubicin | Doxorubicin liposomal |
| Droxia | DTIC | DTIC-Dome |
| Duralone | Efudex | Eligard |
| Ellence | Eloxatin | Elspar |
| Emcyt | Epirubicin | Epoetin alfa |
| Erbitux | *Erwinia* L-asparaginase | Estramustine |
| Ethyol | Etopophos | Etoposide |
| Etoposide phosphate | Eulexin | Evista |
| Exemestane | Fareston | Faslodex |
| Femara | Filgrastim | Floxuridine |
| Fludara | Fludarabine | Fluoroplex |
| Fluorouracil | Fluorouracil (cream) | Fluoxymesterone |
| Flutamide | Folinic Acid | FUDR |
| Fulvestrant | G-CSF | Gefitinib |
| Gemcitabine | Gemtuzumab ozogamicin | Gemzar |
| Gleevec | Lupron | Lupron Depot |
| Matulane | Maxidex | Mechlorethamine |
| Mechlorethamine Hydrochlorine | Medralone | Medrol |
| Megace | Megestrol | Megestrol Acetate |
| Melphalan | Mercaptopurine | Mesna |
| Mesnex | Methotrexate | Methotrexate Sodium |
| Methylprednisolone | Mylocel | Letrozole |
| | Neosar | Neulasta |
| Neumega | Neupogen | Nilandron |
| Nilutamide | Nitrogen Mustard | Novaldex |
| Novantrone | Octreotide | Octreotide acetate |
| Oncospar | Oncovin | Ontak |
| Onxal | Oprevelkin | Orapred |
| Orasone | Oxaliplatin | Paclitaxel |
| Pamidronate | Panretin | Paraplatin |
| Pediapred | PEG Interferon | Pegaspargase |
| Pegfilgrastim | PEG-INTRON | PEG-L-asparaginase |
| Phenylalanine Mustard | Platinol | Platinol-AQ |
| Prednisolone | Prednisone | Prelone |
| Procarbazine | PROCRIT | Proleukin |
| Prolifeprospan 20 with Carmustine implant | Purinethol | Raloxifene |
| Rheumatrex | Rituxan | Rituximab |
| Roveron-A (interferon alfa-2a) | Rubex | Rubidomycin hydrochloride |
| Sandostatin | Sandostatin LAR | Sargramostim |
| Solu-Cortef | Solu-Medrol | STI-571 |
| Streptozocin | Tamoxifen | Targretin |
| Taxol | Taxotere | Temodar |
| Temozolomide | Teniposide | TESPA |
| Thalidomide | Thalomid | TheraCys |
| Thioguanine | Thioguanine Tabloid | Thiophosphoamide |
| Thioplex | Thiotepa | TICE |
| Toposar | Topotecan | Toremifene |
| Trastuzumab | Tretinoin | Trexall |
| Trisenox | TSPA | VCR |
| Velban | Velcade | VePesid |
| Vesanoid | Viadur | Vinblastine |
| Vinblastine Sulfate | Vincasar Pfs | Vincristine |
| Vinorelbine | Vinorelbine tartrate | VLB |
| VP-16 | Vumon | Xeloda |
| Zanosar | Zevalin | Zinecard |
| Zoladex | Zoledronic acid | Zometa |
| Gliadel wafer | Glivec | GM-CSF |

TABLE 1-continued

Examples of Chemotherapeutic Agents

| | | |
|---|---|---|
| Goserelin | granulocyte - colony stimulating factor | Granulocyte macrophage colony stimulating factor |
| Halotestin | Herceptin | Hexadrol |
| Hexalen | Hexamethyl-melamine | HMM |
| Hycamtin | Hydrea | Hydrocort Acetate |
| Hydrocortisone | Hydrocortisone sodium phosphate | Hydrocortisone sodium succinate |
| Hydrocortone phosphate | Hydroxyurea | Ibritumomab |
| Ibritumomab Tiuxetan | Idamycin | Idarubicin |
| Ifex | IFN-alpha | Ifosfamide |
| IL-2 | IL-11 | Imatinib mesylate |
| Imidazole Carboxamide | Interferon alfa | Interferon Alfa-2b (PEG conjugate) |
| Interleukin-2 | Interleukin-11 | Intron A (interferon alfa-2b) |
| Leucovorin | Leukeran | Leukine |
| Leuprolide | Leurocristine | Leustatin |
| Liposomal Ara-C | Liquid Pred | Lomustine |
| L-PAM | L-Sarcolysin | Meticorten |
| Mitomycin | Mitomycin-C | Mitoxantrone |
| M-Prednisol | MTC | MTX |
| Mustargen | Mustine | Mutamycin |
| Myleran | Iressa | Irinotecan |
| Isotretinoin | Kidrolase | Lanacort |
| L-asparaginase | LCR | |

Additional agents that can co-administered to a patient in the same or as a separate formulation include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered.

The subject invention also provides an article of manufacture useful in treating cancer. The article contains a pharmaceutical composition containing a substituted amino-propanol compound, and a pharmaceutically acceptable carrier or diluent. The article of manufacture can be, for example, a vial, bottle, intravenous bag, syringe, nasal applicator, microdialysis probe, or other container for the pharmaceutical composition. The nasal applicator containing the pharmaceutical composition of the invention can further comprise a propellent. The article of manufacture can further comprise packaging. The article of manufacture can also include printed material disclosing instructions for concerning administration of the pharmaceutical composition for the treatment of cancer. Preferably, the printed material discloses instructions concerning administration of the pharmaceutical composition for the treatment of cancer. The printed material can be embossed or imprinted on the article of manufacture and indicate the amount or concentration of the active agent (substituted amino-propanol compound), recommended doses for treatment of the cancer, or recommended weights of individuals to be treated.

As used herein, the terms "cancer" and "cancerous" refer to or describe the physiological condition in mammals that is typically characterized by unregulated cell growth, i.e., proliferative disorders. Examples of such proliferative disorders include cancers such as carcinoma, lymphoma, blastoma, sarcoma, and leukemia, as well as other cancers disclosed herein. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some preferred embodiments the cancer to be treated is mammalian hepatocellular carcinoma, osteosarcoma, breast cancer, ovarian cancer, and/or colon cancer.

Other non-limiting examples of cancers are basal cell carcinoma, biliary tract cancer; bone cancer; breast cancer; brain and CNS cancer; choriocarcinoma; colon cancer; connective tissue cancer; esophageal cancer; eye cancer; cancer of the head and neck; gastric cancer; intra-epithelial neoplasm; larynx cancer; lung cancer; lymphoma including Hodgkin's and Non-Hodgkin's lymphoma; melanoma; myeloma; neuroblastoma; oral cavity cancer (e.g., lip, tongue, mouth, and pharynx); pancreatic cancer; retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site.

As used herein, the terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state.

As used herein, the term "(therapeutically) effective amount" refers to an amount of an agent (e.g., a drug) effective to treat a disease or disorder in a patient. In the case of cancer, the therapeutically effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" refers to an amount which inhibits growth of a target cell, such as a tumor cell, either in vitro or in vivo, irrespective of the mechanism by which cell growth is inhibited. In a preferred embodiment, the growth inhibitory amount inhibits growth of the target cell in cell culture by greater than about 20%, preferably greater than about 50%, most preferably greater than about 75% (e.g. from about 75% to about 100%).

The terms "cell" and "cells" are used interchangeably herein and are intended to include either a single cell or a plurality of cells unless otherwise specified.

As used herein, the term "pharmaceutically acceptable salt or prodrug" is intended to describe any pharmaceutically acceptable form (such as an ester, phosphate ester, salt of an ester or a related group) of a substituted amino-propanol compound, which, upon administration to a patient, provides the substituted amino-propanol compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "pharmaceutically acceptable esters" as used herein, unless otherwise specified, includes those esters of one or more compounds, which are, within the scope of sound medical judgment, suitable for use in contact with the tissues of hosts without undue toxicity, irritation, allergic response and the like, are commensurate with a reasonable benefit/risk ratio, and are effective for their intended use.

The following embodiments, among others, are included in this invention:

Embodiment 1

A compound that has the formula

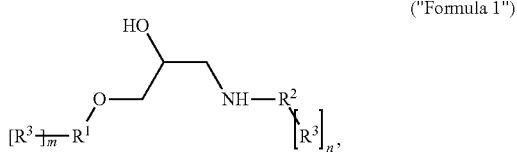

("Formula 1")

or a pharmaceutically acceptable salt thereof, wherein:
$R^1$ is ($C_1$-$C_{30}$) aliphatic,
$R^2$ is ($C_1$-$C_{30}$) aliphatic,
m and n are independently 0-3, and
each substituent $R^3$ that is present independently consists of 1-10 non-hydrogen atoms along with 0 or more hydrogen atoms.

"Aliphatic" as used herein means a hydrocarbon (containing only carbon and hydrogen atoms) that may be saturated or unsaturated, but is not aromatic. "Aliphatic" as used herein encompasses hydrocarbons that contain non-aromatic cyclic structures (for example, a cycloalkyl group).

Embodiment 2

The compound or pharmaceutically acceptable salt thereof according to embodiment 1 wherein $R^1$:

(i) contains no annulation, or
(ii) contains 1 annulation, or
(iii) contains 2 annulations, or
(iv) contains 3 annulations, or
(v) contains 4 or more annulations.

"Annulation" as used herein refers to creating a cyclic structure. A molecule that contains no cyclic structures of any type contains no annulation. A molecule containing 1 annulation means a molecule that contains a single simple ring. One of skill in the art would readily recognize that the following structures, for example, each contain a simple ring:

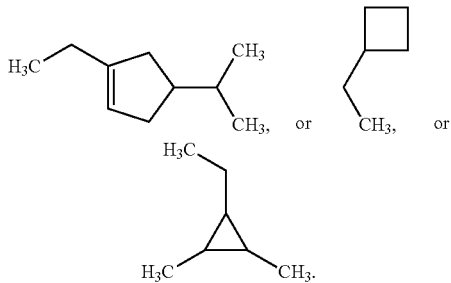

Rings containing 3, 4, 5, 6, 7, 8, or more atoms are contemplated. A molecule containing two annulations is any molecule that could conceptually be created by adding a bridging structure (a bond, a bivalent atom, or a bivalent straight or branched chain) to connect two different parts of a molecule already having one annulation such that an additional cyclic structure is formed. For example, the following molecules, respectively, could conceptually be created by adding a bridging bond to the three simple ring structures used as examples above:

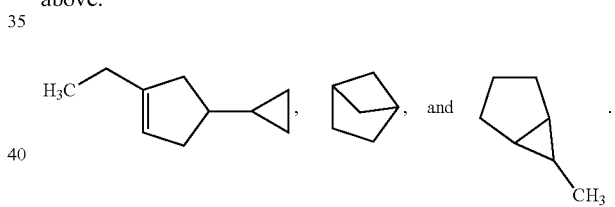

These molecules thus have 2 annulations. In like manner, a molecule with (i+1) annulations is any molecule that could conceptually be created by adding a bridging structure (a bond, a divalent atom, or a divalent straight or branched chain) to connect two different parts of a molecule with (i) annulations such that an additional cyclic structure is formed. In case of any ambiguity as to how many "annulations" a given molecule has, the molecule shall be deemed to have the lowest of the possible number of annulations.

Embodiment 3

The compound or pharmaceutically acceptable salt thereof according to embodiments 1-2 wherein $R^1$:
(i) contains no branch points, or
(ii) contains 1 branch point, or
(iii) contains 2 branch points, or
(iv) contains 3 branch points, or
(v) contains 4 branch points, or
(vi) contains 5 branch points, or
(vii) contains 6 branch points, or
(viii) contains 7 branch points, or
(ix) contains 8 branch points, or
(x) contains 9 or more branch points.

As used herein, branch points are calculated by counting each tertiary carbon once and counting each quaternary carbon twice. Thus

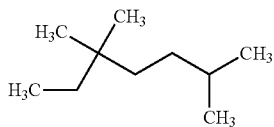

contains 3 branch points (one quaternary carbon and one tertiary carbon). As used herein, a tertiary carbon is a carbon that is bonded to three other carbons and a quaternary carbon is a carbon that is bonded to four other carbons. For the purposes of counting the number of branch points contained in $R^1$ or $R^2$, substitution with $R^3$ is not deemed to create additional branch points.

Embodiment 4

The compound or pharmaceutically acceptable salt thereof according to embodiments 1-3 wherein $R^1$:
(i) contains no carbon-carbon double bond, or
(ii) contains 1 carbon-carbon double bond, or
(iii) contains 2 carbon-carbon double bonds, or
(iv) contains 3 carbon-carbon double bonds, or
(v) contains 4 carbon-carbon double bonds, or
(vi) contains 5 carbon-carbon double bonds, or
(vii) contains 6 carbon-carbon double bonds, or
(viii) contains 7 carbon-carbon double bonds, or
(ix) contains 8 carbon-carbon double bonds, or
(x) contains 9 or more carbon-carbon double bonds.

Embodiment 5

The compound or pharmaceutically acceptable salt thereof according to embodiments 1-4 wherein $R^1$:
(i) contains no carbon-carbon triple bond, or
(ii) contains 1 carbon-carbon triple bond, or
(iii) contains 2 carbon-carbon triple bonds, or
(iv) contains 3 carbon-carbon triple bonds, or
(v) contains 4 carbon-carbon triple bonds, or
(vi) contains 5 carbon-carbon triple bonds, or
(vii) contains 6 carbon-carbon triple bonds, or
(viii) contains 7 carbon-carbon triple bonds, or
(ix) contains 8 carbon-carbon triple bonds, or
(x) contains 9 or more carbon-carbon triple bonds.

Embodiment 6

The compound or pharmaceutically acceptable salt thereof according to embodiments 1-5 wherein $R^1$:
(i) is $C_1$ aliphatic, or
(ii) is $C_2$ aliphatic, or
(iii) is $C_3$ aliphatic, or
(iv) is $C_4$ aliphatic, or
(v) is $C_5$ aliphatic, or
(vi) is $C_6$ aliphatic, or
(vii) is $C_7$ aliphatic, or
(viii) is $C_8$ aliphatic, or
(ix) is $C_9$ aliphatic, or
(x) is $C_{10}$ aliphatic, or
(xi) is $C_{11}$ aliphatic, or
(xii) is $C_{12}$ aliphatic, or
(xiii) is $C_{13}$ aliphatic, or
(xiv) is $C_{14}$ aliphatic, or
(xv) is $C_{15}$ aliphatic, or
(xvi) is $C_{16}$ aliphatic, or
(xvii) is $C_{17}$ aliphatic, or
(xviii) is $C_{18}$ aliphatic, or
(xix) is $C_{19}$ aliphatic, or
(xx) is $C_{20}$ aliphatic, or
(xxi) is $C_{21}$ aliphatic, or
(xxii) is $C_{22}$ aliphatic, or
(xxiii) is $C_{23}$ aliphatic, or
(xxiv) is $C_{24}$ aliphatic, or
(xxv) is $C_{25}$ aliphatic, or
(xxvi) is $C_{26}$ aliphatic, or
(xxvii) is $C_{27}$ aliphatic, or
(xxviii) is $C_{28}$ aliphatic, or
(xxix) is $C_{29}$ aliphatic, or
(xxx) is $C_{30}$ aliphatic.

Embodiment 7

The compound or pharmaceutically acceptable salt thereof according to embodiments 1-6 wherein $R^2$:
(i) contains no annulation, or
(ii) contains 1 annulation, or
(iii) contains 2 annulations, or
(iv) contains 3 annulations, or
(v) contains 4 or more annulations.

Embodiment 8

The compound or pharmaceutically acceptable salt thereof according to embodiments 1-7 wherein $R^2$:
(i) contains no branch points, or
(ii) contains 1 branch point, or
(iii) contains 2 branch points, or
(iv) contains 3 branch points, or
(v) contains 4 branch points, or
(vi) contains 5 branch points, or
(vii) contains 6 branch points, or
(viii) contains 7 branch points, or
(ix) contains 8 branch points, or
(x) contains 9 or more branch points.

Embodiment 9

The compound or pharmaceutically acceptable salt thereof according to embodiments 1-8 wherein $R^2$:
(i) contains no carbon-carbon double bond, or
(ii) contains 1 carbon-carbon double bond, or
(iii) contains 2 carbon-carbon double bonds, or
(iv) contains 3 carbon-carbon double bonds, or
(v) contains 4 carbon-carbon double bonds, or
(vi) contains 5 carbon-carbon double bonds, or
(vii) contains 6 carbon-carbon double bonds, or
(viii) contains 7 carbon-carbon double bonds, or
(ix) contains 8 carbon-carbon double bonds, or
(x) contains 9 or more carbon-carbon double bonds.

Embodiment 10

The compound or pharmaceutically acceptable salt thereof according to embodiments 1-9 wherein $R^2$:
(i) contains no carbon-carbon triple bond, or
(ii) contains 1 carbon-carbon triple bond, or
(iii) contains 2 carbon-carbon triple bonds, or
(iv) contains 3 carbon-carbon triple bonds, or
(v) contains 4 carbon-carbon triple bonds, or (vi) contains 5 carbon-carbon triple bonds, or
(vii) contains 6 carbon-carbon triple bonds, or
(viii) contains 7 carbon-carbon triple bonds, or
(ix) contains 8 carbon-carbon triple bonds, or
(x) contains 9 or more carbon-carbon triple bonds.

Embodiment 11

The compound or pharmaceutically acceptable salt thereof according to embodiments 1-10 wherein $R^2$:
(i) is $C_1$ aliphatic, or
(ii) is $C_2$ aliphatic, or
(iii) is $C_3$ aliphatic, or
(iv) is $C_4$ aliphatic, or
(v) is $C_5$ aliphatic, or
(vi) is $C_6$ aliphatic, or
(vii) is $C_7$ aliphatic, or
(viii) is $C_8$ aliphatic, or
(ix) is $C_9$ aliphatic, or
(x) is $C_{10}$ aliphatic, or
(xi) is $C_{11}$ aliphatic, or
(xii) is $C_{12}$ aliphatic, or
(xiii) is $C_{13}$ aliphatic, or
(xiv) is $C_{14}$ aliphatic, or
(xv) is $C_{15}$ aliphatic, or
(xvi) is $C_{16}$ aliphatic, or
(xvii) is $C_{17}$ aliphatic, or
(xviii) is $C_{18}$ aliphatic, or
(xix) is $C_{19}$ aliphatic, or
(xx) is $C_{20}$ aliphatic, or
(xxi) is $C_{21}$ aliphatic, or
(xxii) is $C_{22}$ aliphatic, or
(xxiii) is $C_{23}$ aliphatic, or
(xxiv) is $C_{24}$ aliphatic, or
(xxv) is $C_{25}$ aliphatic, or
(xxvi) is $C_{26}$ aliphatic, or
(xxvii) is $C_{27}$ aliphatic, or
(xxviii) is $C_{28}$ aliphatic, or
(xxix) is $C_{29}$ aliphatic, or
(xxx) is $C_{30}$ aliphatic.

Embodiment 12

The compound or pharmaceutically acceptable salt thereof according to embodiments 1-11, wherein m:
(i) is zero, or
(ii) is one, or
(iii) is two, or
(iv) is three.

Embodiment 13

The compound or pharmaceutically acceptable salt thereof according to embodiments 1-12, wherein each $R^3$ substituted on $R^1$:
(i) contains at most a single non-hydrogen atom, or
(ii) contains at most 2 non-hydrogen atoms, or
(iii) contains at most 3 non-hydrogen atoms, or
(iv) contains at most 4 non-hydrogen atoms, or
(v) contains at most 5 non-hydrogen atoms, or
(vi) contains at most 6 non-hydrogen atoms, or
(vii) contains at most 7 non-hydrogen atoms, or
(viii) contains at most 8 non-hydrogen atoms, or
(ix) contains at most 9 non-hydrogen atoms, or
(x) contains at most 10 non-hydrogen atoms.

Embodiment 14

The compound or pharmaceutically acceptable salt thereof according to embodiments 1-13, wherein n:
(i) is zero, or
(ii) is one, or
(iii) is two, or
(iv) is three.

Embodiment 15

The compound or pharmaceutically acceptable salt thereof according to embodiments 1-14, wherein each $R^3$ substituted on $R^2$:
(i) contains at most a single non-hydrogen atom, or
(ii) contains at most 2 non-hydrogen atoms, or
(iii) contains at most 3 non-hydrogen atoms, or
(iv) contains at most 4 non-hydrogen atoms, or
(v) contains at most 5 non-hydrogen atoms, or
(vi) contains at most 6 non-hydrogen atoms, or
(vii) contains at most 7 non-hydrogen atoms, or
(viii) contains at most 8 non-hydrogen atoms, or
(ix) contains at most 9 non-hydrogen atoms, or
(x) contains at most 10 non-hydrogen atoms.

Embodiment 16

The compound or pharmaceutically acceptable salt thereof according to embodiments 1-15, wherein for each $R^3$ substituted on $R^1$:
(i) each non-hydrogen atom is halogen, C, N, O, P, or S; or
(ii) each non-hydrogen atom is halogen, C, N, O, or P; or
(iii) each non-hydrogen atom is halogen, C, N, O, or S; or
(iv) each non-hydrogen atom is halogen, C, N, P, or S; or
(v) each non-hydrogen atom is halogen, C, O, P, or S; or
(vi) each non-hydrogen atom is halogen, N, O, P, or S; or
(vii) each non-hydrogen atom is C, N, O, P, or S.

While certain embodiments have been explicitly set forth here, other embodiments are specifically contemplated wherein the non-hydrogen atoms contained within $R^3$ are limited to any one type of atom selected from the group consisting of halogen, C, N, O, P, and S (for example, limited to N or limited to O); any two types of atom selected from the group consisting of halogen, C, N, O, P, and S (for example, limited to P and O, or limited to S and O); any three types of atom selected from the group consisting of halogen, C, N, O, P, and S (for example, limited to C, N, and O, or limited to C, O, and halogen); or any four types of atom selected from the group consisting of halogen, C, N, O, P, and S. It is further contemplated that such limitations may also be applied to $R^3$ substituted on. $R^2$, and such application may be separate and independent from any such limitation applied to $R^3$ substituted on $R^1$.

Embodiment 17

The compound or pharmaceutically acceptable salt thereof according to embodiments 1-16, wherein for each $R^3$ substituted on $R^2$:
(i) each non-hydrogen atom is halogen, C, N, O, P, or S; or
(ii) each non-hydrogen atom is halogen, C, N, O, or P; or
(iii) each non-hydrogen atom is halogen, C, N, O, or S; or
(iv) each non-hydrogen atom is halogen, C, N, P, or S; or
(v) each non-hydrogen atom is halogen, C, O, P, or S; or
(vi) each non-hydrogen atom is halogen, N, O, P, or S; or
(vii) each non-hydrogen atom is C, N, O, P, or S.

Embodiment 18

The compound or pharmaceutically acceptable salt thereof according to embodiments 1-17, wherein no $R^3$ substituted on $R^1$ contains an aryl group.

As used herein, "aryl" means a carbocyclic aromatic group, for example phenyl or naphthyl; hence "aryl" does not encompass "heteroaryl".

Embodiment 19

The compound or pharmaceutically acceptable salt thereof according to embodiments 1-18, wherein no R³ substituted on R¹ contains a heteroaryl group.

As used herein, "heteroaryl" means a heterocyclic aromatic group, for example pyridyl.

Embodiment 20

The compound or pharmaceutically acceptable salt thereof according to embodiments 1-19, wherein no R³ substituted on R² contains an aryl group.

Embodiment 21

The compound or pharmaceutically acceptable salt thereof according to embodiments 1-20, wherein no R³ substituted on R² contains a heteroaryl group.

Embodiment 22

The compound or pharmaceutically acceptable salt thereof of embodiment 1, wherein R¹ is hexadecenyl, hexadecyl, or octyl; R² is isopropyl; and neither R¹ nor R² is substituted with any substituent R³.

Embodiment 23

The compound or pharmaceutically acceptable salt thereof of embodiment 1, wherein said compound is:

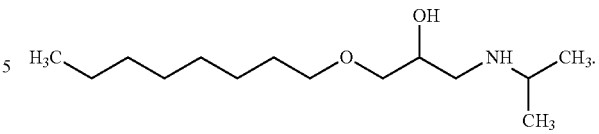

Embodiment 24

The compound or pharmaceutically acceptable salt thereof of embodiment 1, wherein said compound is:

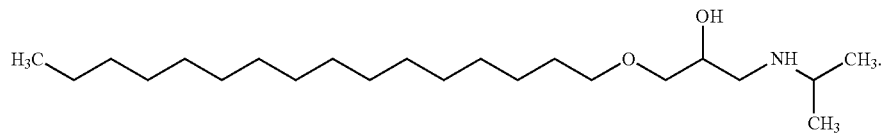 [SMILES: CCCCCCCCCCCCCCCCOCC(O)CNC(C)C]

Embodiment 25

The compound or pharmaceutically acceptable salt thereof of embodiment 1, wherein said compound is:

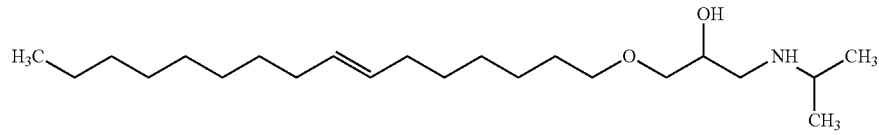 [SMILES: CCCCCCCC/C=C/CCCCCCOCC(O)CNC(C)C]

or the cis isomer thereof.

Embodiment 26

A method for treating cancer in a patient, said method comprising: administering the compound or pharmaceutically acceptable salt thereof of any of embodiments 1-25 to a patient with cancer.

Embodiment 27

A method for treating cancer in a patient, said method comprising: administering an LPL-GPCR antagonist to a patient with cancer.

Embodiment 28

The method of embodiment 27, wherein the antagonist is an antagonist of G2A, GPR4, or ORG-1.

Embodiment 29

The method of any of embodiments 26-28, further comprising identifying the patient as suffering from a cancer treatable by modulation of signaling at one or more LPL-GPCRs.

Embodiment 30

The method of any of embodiments 26-29 wherein the cancer is mammalian hepatocellular carcinoma, osteosarcoma, breast cancer, colon cancer, or ovarian cancer.

Embodiment 31

The method of any of embodiments 26-30, wherein said administering is carried out at least in part for the purpose of inhibiting cancer cell growth.

Embodiment 32

The method of any of embodiments 26-31, wherein the patient is suffering from a tumor and the compound or pharmaceutically acceptable salt thereof inhibits growth of the tumor.

Embodiment 33

The method of any of embodiments 26-32, wherein the route of administration is topical, intravenous, intraperitoneal, intramuscular, subcutaneous, oral, intranasal, or inhaled.

Embodiment 34

A pharmaceutical composition comprising the compound or pharmaceutically acceptable salt thereof of any of embodiments 1-25 and a pharmaceutically acceptable carrier, adjuvant, diluent, or excipient.

Embodiment 35

The pharmaceutical composition of embodiment 34, further comprising an immunomodulating agent, an antioxidant, a free radical scavenging agent, a peptide, a growth factor, an antibiotic, a bacteriostatic agent, an immunosuppressive agent, an anticoagulant, a buffering agent, an anti-inflammatory agent, an anti-pyretic, a time-release binder, an anesthetic, a steroid, or a corticosteroid.

Embodiment 36

The pharmaceutical composition of any of embodiments 34-35 wherein the compound or pharmaceutically acceptable salt thereof is present at a therapeutically effective concentration.

Embodiment 37

The pharmaceutical composition of any of embodiments 34-36, further comprising a second active pharmaceutical ingredient (API) in addition to said compound or pharmaceutically acceptable salt thereof.

Embodiment 38

The pharmaceutical composition of embodiment 37, wherein the second API is an anti-cancer agent.

Embodiment 39

A method for treating cancer in a patient, said method comprising: administering a pharmaceutical composition according to any of embodiments 34-38 to a patient with cancer.

With regard to embodiment 39, it is further contemplated that any pharmaceutical composition containing a compound or pharmaceutically acceptable salt thereof of the invention could be administered according to the methods (and limitations) of embodiments 26-33.

All patents, patent applications, provisional applications, and publications referred to or cited herein, supra or infra, are incorporated by reference in their entirety, including all figures and tables, to the extent they are not inconsistent with the explicit teachings of this specification.

EXAMPLE 1

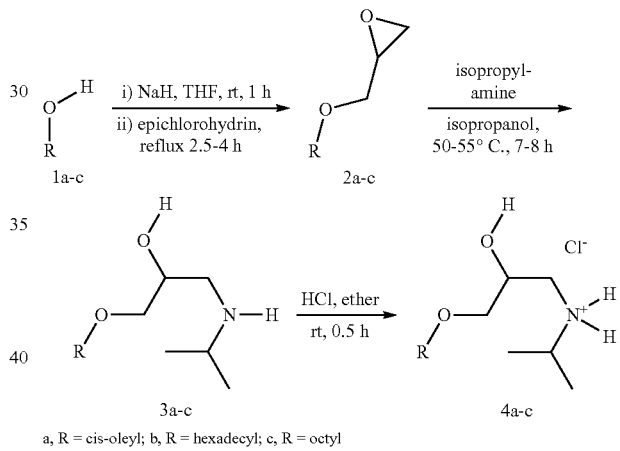

a, R = cis-oleyl; b, R = hexadecyl; c, R = octyl

General Procedure for the Synthesis of
3-alkyloxy(3-alkenyloxy)-1,2-epoxypropanes (2a-c)

A solution of 10 mmol of alcohol 1a-c in 20 mL of dry tetrahydrofuran (THF) was added under nitrogen to a stirred suspension of 10 mmol of sodium hydride (60% oil suspension, previously washed with hexane) at 5-10° C. and the mixture was stirred at room temperature for 0.5 h. Epichlorohydrin (20 mmol) was added to this mixture, which was then heated at reflux for 3-9 h. The solvent was evaporated under reduced pressure. The residue was treated with iced water. The product was extracted with ethyl acetate (3×35 mL) and purified by silica gel column chromatography using $CHCl_3$-hexane (1:2) to give pure 2a-c in 64, 47 and 54% yields, respectively.

2a:
Colorless oil, $^1$H NMR δ (300 MHz, $CDCl_3$, $Me_4Si$) 5.35 (t, J=5.0 Hz, 2H), 3.71 (dd, J=11.4, 3.0 Hz, 1H), 3.55-3.42 (m, 2H), 3.39 (dd, J=11.5, 5.9 Hz, 1H), 3.18-3.12 (m, 1H), 2.82-2.78 (m, 1H), 2.61 (dd, J=5.1, 2.7 Hz, 1H), 2.04-1.98 (m, 4H), 1.63-1.54 (m, 2H), 1.29-1.27 (m, 22H), 0.88 (t, J=6.5 Hz, 3H); $^{13}$C NMR δ (75 MHz, CDCl$_3$, Me$_4$Si) 129.9, 129.8, 71.7, 71.4, 50.9, 44.3, 31.9, 29.8, 29.7, 29.67, 29.5, 29.46, 29.4, 29.3, 29.2, 27.2, 26.0, 22.7, 14.1.

2b:

Colorless microcrystals, mp 27-28° C., $^1$H NMR δ (300 MHz, CDCl$_3$, Me$_4$Si) 3.71 (dd, J=11.4, 3.2 Hz, 1H), 3.55-3.42 (m, 2H), 3.38 (dd, J=11.5, 5.8 Hz, 1H) 3.18-3.13 (m, 1H), 2.82-2.79 (m, 1H), 2.61 (dd, J=4.9, 2.6 Hz, 1H), 1.64-1.54 (m, 2H), 1.28-1.23 (26H), 0.88 (t, J=6.5 Hz, 3H); $^{13}$C NMR δ (75 MHz, CDCl$_3$, Me$_4$Si) 71.7, 71.5, 50.9, 44.4, 31.9, 29.7, 29.65, 29.59 29.46, 29.36, 26.1, 22.7, 14.1.

2c:

Colorless oil, $^1$H NMR δ (300 MHz, CDCl$_3$, Me$_4$Si) 3.71 (dd, J=11.5, 3.2 Hz, 1H), 3.55-3.42 (m, 2H), 3.38 (dd, J=11.5, 5.8 Hz, 1H), 3.18-3.12 (m, 1H), 2.81-2.78 (m, 1H), 2.61 (dd, J=4.9, 2.6 Hz, 1H), 1.63-1.54 (m, 2H), 1.36-1.27 (m, 10H), 0.88 (t, J=6.5 Hz, 3H); $^{13}$C NMR δ (75 MHz, CDCl$_3$, Me$_4$Si) 71.7, 71.4, 50.8, 44.3, 31.8, 29.6, 29.4, 29.2, 26.0, 22.6, 14.0.

EXAMPLE 2

General Procedure for the Synthesis of 1-alkyloxy(1-alkenyloxy)-3-isopropylamino-propan-2-oles (3a-c)

A solution of 4 mmol of oxirane (2a-c) and 32 mmol of isopropylamine in 40 mL of 2-propanol was stirred at 45-55° C. for 7-15 h. The solvent was evaporated under reduced pressure and the residue was purified by recrystallization or chromatography to give pure 3a-c in 83, 86 and 89% yields, respectively.

3a:

Colorless oil, $^1$H NMR δ (300 MHz, CDCl$_3$, Me$_4$Si) 5.35 (t, J=5.2 Hz, 2H), 3.86-3.78 (m, 1H), 3.48-3.37 (m, 4H), 2.83-2.72 (m, 2H), 2.59 (dd, J=11.9, 8.0 Hz, 1H), 2.37 (br s, 1H), 2.04-1.98 (m, 4H), 1.62-1.53 (m, 2H), 1.36-1.27 (m, 22H), 1.07 (d, J=6.2 Hz, 6H), 0.88 (t, J=6.3 Hz, 3H); $^{13}$C NMR δ (75 MHz, CDCl$_3$, Me$_4$Si) 129.9, 129.8, 73.5, 71.6, 69.0, 49.6, 48.8, 31.9, 29.7, 29.6, 29.48, 29.46, 29.4, 29.3, 29.2, 27.2, 26.1, 23.0 22.9, 22.6, 14.1.

3b:

Colorless microcrystals, mp 55-57° C. $^1$H NMR δ (300 MHz, CDCl$_3$, Me$_4$Si) 3.85-3.77 (m, 1H), 3.49-3.37 (m, 4H), 2.83-2.70 (m, 2H), 2.59 (dd, J=11.9, 7.8 Hz, 1H), 1.62-1.53 (m, 2H), 1.27-1.24 (m, 26H), 1.06 (d, J=6.0 Hz, 6H), 0.88 (t, J=6.2 Hz, 3H); $^{13}$C NMR (75 MHz, CDCl$_3$, Me$_4$Si) 73.5, 71.7, 69.1, 49.6, 48.8, 31.9, 29.7, 29.6, 29.5, 29.4, 26.1, 23.1, 23.0, 22.7, 14.1.

3c:

Colorless oil, $^1$H NMR δ (300 MHz, CDCl$_3$, Me$_4$Si) 3.87-3.79 (m, 1H), 3.47-3.37 (m, 4H), 2.83-2.71 (m, 2H), 2.58 (dd, J=12.0, 8.1 Hz, 1H), 1.62-1.53 (m, 2H), 1.29-1.27 (m, 10H), 1.06 (d, J=6.2 Hz, 6H), 0.88 (t, J=6.5 Hz, 3H); $^{13}$C NMR δ (75 MHz, CDCl$_3$, Me$_4$Si) 73.6, 71.6, 68.9, 49.7, 48.7, 31.7, 29.5, 29.3, 29.2, 26.0, 22.9, 22.6, 14.0.

EXAMPLE 3

General Procedure for the Synthesis of 1-alkyloxy(1-alkenyloxy)-3-isopropylamino-propan-2-ol hydrochlorides (4a-c)

1-Alkyloxy(1-alkenyloxy)-3-isopropylamino-propan-2-ol (3a-c) (2 mmol) was dissolved in ether (35 mL) and hydrochloric acid (4 mmol, 2M solution in ether) was added dropwise at 5-10° C. with stirring. The reaction mixture was stirred for additional 0.5 h. The solid was filtered and washed with ether (for 4b) or the solvent was evaporated from reaction mixture under reduced pressure (for 4a,c) to give pure hydrochloride in 90, 95 and 94% yields, respectively.

4a:

Brownish microcrystals, mp 37-38° C., $^1$H NMR δ (300 MHz, DMSO-d$_6$, Me$_4$Si) 8.96 (br s, 1H), 8.52 (br s, 1H), 5.34 (t, J=4.8 Hz, 2H), 4.02-3.74 (m, 1H), 3.42-3.28 (m, 5H), 3.01-2.94 (m, 1H), 2.83-2.74 (m, 1H), 2.02-1.95 (m, 4H), 1.53-1.45 (m, 2H), 1.32-1.22 (m, 28H), 0.86 (t, J=6.0 Hz, 3H); $^{13}$C NMR δ (75 MHz, DMSO, Me$_4$Si) 129.6, 72.4, 70.7, 65.5, 49.7, 47.1, 31.3, 29.13, 29.08, 28.92, 28.8, 28.7, 28.62, 28.58, 26.59, 26.55, 25.6, 22.1, 18.6, 18.1, 13.9.

4b:

Rose microcrystals, mp 75-77° C.,

4c:

Yellowish oil.

EXAMPLE 4

In preliminary studies, it was found that hexadecyloxy-, octadecenyloxy- and octyloxy-derivatives of isopropylamino propanol hydrochloride (AIP) effectively blocked proliferation/survival of human hepatocellular carcinoma cell line HUH-7 in culture (FIG. 6A-C). By contrast, it was found that AIDS did not affect significantly primary rat hepatocytes at concentrations (50 µM) effective to kill all tumor cells (FIG. 7A-C). Additionally, human primary hepatocytes, obtained from a donor (ADMET Technologies) who did not exhibit liver pathology, hexadecyloxy- and octadecenyloxy analogs did not produce significant cytotoxic effects at 20 µM and had a modest effect at 50 µM (FIG. 8A-C). Again, at 20-50 µM all HUH-7 hepatocellular carcinoma cells died according to MTS test and microscopy data. This opens the window for potential therapeutic intervention being non- or less toxic for residual normal hepatocytes. Similar results were observed for breast cancer cell lines (FIG. 9A-D), human and canine osteosarcoma cell lines (FIGS. 10A-F and 11A-D, respectively).

We claim:

1. A compound or pharmaceutically acceptable salt thereof, wherein the compound has the formula:

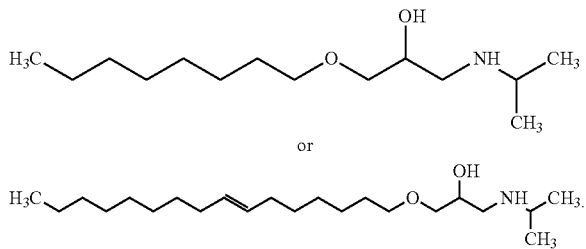

2. The compound or pharmaceutically acceptable salt thereof of claim 1, wherein said compound is:

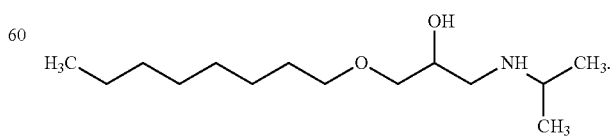

3. The compound or pharmaceutically acceptable salt thereof of claim 1, wherein said compound is:

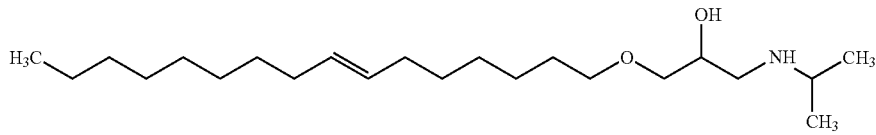 [SMILES: CCCCCCCC/C=C/CCCCCCOCC(O)CNC(C)C]

or the cis isomer thereof.

4. A composition comprising a combination of two or more compounds selected from the group consisting of:

a) H₃C~~~~~O~CH(OH)~CH₂~NH~CH(CH₃)₂;

b) H₃C~~~~~O~CH(OH)~CH₂~NH~CH(CH₃)₂; and c) H₃C~~~=~~~O~CH(OH)~CH₂~NH~CH(CH₃)₂ or the cis isomer thereof.

5. A pharmaceutical composition comprising a compound according to claim 1 and a pharmaceutically acceptable carrier, adjuvant, diluent, or excipient.

6. The pharmaceutical composition of claim 5, further comprising an immunomodulating agent, an antioxidant, a free radical scavenging agent, a peptide, a growth factor, an antibiotic, a bacteriostatic agent, an immunosuppressive agent, an anticoagulant, a buffering agent, an anti-inflammatory agent, an anti-pyretic, a time-release binder, an anesthetic, a steroid, or a corticosteroid.

7. The pharmaceutical composition of claim 5, further comprising a second active pharmaceutical ingredient (API) in addition to said compound or pharmaceutically acceptable salt thereof.

8. The pharmaceutical composition of claim 7, wherein the second API is an anti-cancer agent.

9. A pharmaceutical composition comprising a composition according to claim 4 and a pharmaceutically acceptable carrier, adjuvant, diluent, or excipient.

10. The pharmaceutical composition of claim 9, further comprising an immunomodulating agent, an antioxidant, a free radical scavenging agent, a peptide, a growth factor, an antibiotic, a bacteriostatic agent, an immunosuppressive agent, an anticoagulant, a buffering agent, an anti-inflammatory agent, an anti-pyretic, a time-release binder, an anesthetic, a steroid, or a corticosteroid.

11. The pharmaceutical composition of claim 9, further comprising a second active pharmaceutical ingredient (API) in addition to said compound or pharmaceutically acceptable salt thereof.

12. The pharmaceutical composition of claim 11, wherein the second API is an anti-cancer agent.

\* \* \* \* \*

UNITED STATES PATENT AND TRADEMARK OFFICE
CERTIFICATE OF CORRECTION

PATENT NO.         : 8,871,983 B2
APPLICATION NO.    : 13/057793
DATED              : October 28, 2014
INVENTOR(S)        : Stanislav I. Svetlov and Anatoliy Vakulenko Page 1 of 1

It is certified that error appears in the above-identified patent and that said Letters Patent is hereby corrected as shown below:

In the Specification,

Column 1,
Lines 4-6, "This invention was made with government support under National Science Foundation grant number 1R21DK061649-01. The government has certain rights in the invention." should read
--This invention was made with government support under grant number 1R21DK061649-01 awarded by National Institutes of Health. The government has certain rights in the invention.--.

Column 4,
Line 62, "in and n" should read --m and n--.

Column 13,
Line 27, "can co-administered" should read --can be co-administered--.
Lines 51-52, "instructions for concerning administration" should read
--instructions for administration--.

Column 25,
Line 9, "1.28-1.23 (26H)" should read --1.28-1.23 (m, 26H)--.

Column 26,
Line 25, "AIDS did" should read --AIPS did--.

Signed and Sealed this
Seventeenth Day of February, 2015

Michelle K. Lee
*Deputy Director of the United States Patent and Trademark Office*